(12) United States Patent
Yacoby et al.

(10) Patent No.: US 9,702,900 B2
(45) Date of Patent: Jul. 11, 2017

(54) METHOD AND SYSTEM FOR MAGNETIC RESONANCE IMAGING USING NITROGEN-VACANCY CENTERS

(71) Applicants: President and Fellows of Harvard College, Cambridge, MA (US); University College London, London (GB)

(72) Inventors: Amir Yacoby, Newton, MA (US); Michael Grinolds, Palo Alto, CA (US); Marc Warner, Bedford (GB); Kristiaan De Greve, Cambridge, MA (US); Yuliya Dovzhenko, Cambridge, MA (US)

(73) Assignees: President and Fellows of Harvard College, Cambridge, MA (US); University College London, London (GB)

(*) Notice: Subject to any disclaimer, the term of this patent is extended or adjusted under 35 U.S.C. 154(b) by 189 days.

(21) Appl. No.: 14/721,065

(22) Filed: May 26, 2015

(65) Prior Publication Data
US 2017/0038411 A1 Feb. 9, 2017

Related U.S. Application Data

(60) Provisional application No. 62/103,234, filed on Jan. 14, 2015.

(51) Int. Cl.
*G01Q 60/52* (2010.01)
*G01R 33/62* (2006.01)
*G01R 33/24* (2006.01)

(52) U.S. Cl.
CPC ............ *G01Q 60/52* (2013.01); *G01R 33/24* (2013.01); *G01R 33/62* (2013.01)

(58) Field of Classification Search
CPC ........ G01Q 60/52; G01Q 60/50; G01R 33/20; G01R 33/24; G01R 33/62
See application file for complete search history.

(56) References Cited

U.S. PATENT DOCUMENTS

2010/0308813 A1* 12/2010 Lukin .................. G01R 33/032
324/244.1

OTHER PUBLICATIONS

Grinolds et al., 'Nanoscale magnetic imaging of a single electron spin under ambient conditions' Feb. 3, 2013, Nature Physics, vol. 9, pp. 215-219.*

(Continued)

*Primary Examiner* — Wyatt Stoffa
*Assistant Examiner* — Eliza Osenbaugh-Stewar
(74) *Attorney, Agent, or Firm* — Wilmer Cutler Pickering Hale and Dorr LLP (57) ABSTRACT

A method for performing sub-nanometer three-dimensional magnetic resonance imaging of a sample under ambient conditions using a diamond having at least one shallowly planted nitrogen-vacancy (NV) center. A driving radio-frequency (RF) signal and a microwave signal are applied to provide independent control of the NV spin and the target dark spins. A magnetic-field gradient is applied to the sample with a scanning magnetic tip to provide a narrow spatial volume in which the target dark electronic spins are on resonance with the driving RF field. The sample is controllably scanned by moving the magnetic tip to systematically bring non-resonant target dark spins into resonance with RF signal. The dark spins are measured and mapped by detecting magnetic resonance of said nitrogen-vacancy center at each of said different magnetic tip positions. The dark-spin point-spread-function for imaging the dark spins is directly measured by the NV center.

6 Claims, 8 Drawing Sheets (56) References Cited

OTHER PUBLICATIONS

Balasubramanian et al., 'Nanoscale imaging magnetometry with diamond spins under ambient conditions' Oct. 2, 2008, Nature, vol. 455, pp. 648-651.*

* cited by examiner

METHOD AND SYSTEM FOR MAGNETIC RESONANCE IMAGING USING NITROGEN-VACANCY CENTERS

CROSS-REFERENCE TO RELATED APPLICATIONS

The present application claims the benefit of the filing date of U.S. Provisional Patent Application Ser. No. 62/103,234 filed by the present inventors on Jan. 14, 2015.

The aforementioned provisional patent application is hereby incorporated by reference in its entirety.

STATEMENT REGARDING FEDERALLY SPONSORED RESEARCH OR DEVELOPMENT

This invention was made with government support under Contract No. HR0011-11-C-0073 awarded by the Defense Advanced Research Projects Agency (DARPA), Contract No. 5710003135 awarded by Office of Naval Research and Contract No. HR0011-09-1-0005 awarded by the Defense Advanced Research Projects Agency (DARPA). The government has certain rights in the invention.

BACKGROUND OF THE INVENTION

Field of the Invention

The present invention relates to magnetic resonance imaging (MRI), and more particularly, to methods and systems for sub-nanometer magnetic resonance imaging.

Brief Description of the Related Art

Magnetic resonance imaging (MRI) has revolutionized biomedical science by providing non-invasive, three-dimensional biological imaging. See, Mansfield, P. "Snapshot magnetic resonance imaging (Nobel lecture)," Angew Chem Int Ed Engl. 2004; 43:5456-5464. However, spatial resolution in conventional MRI systems is limited to tens of microns, which is insufficient for imaging on molecular and atomic scales. See, P. Glover and P. Mansfield, "Limits to magnetic resonance microscopy," Rep. Prog. Phys. 65, 1489 (2002).

Atomic-scale magnetic resonance imaging (MRI) would have wide-ranging applications including determining the structure of individual biomolecules, imaging the dynamics of bottom-up molecular engineering, and achieving site-resolved readout in solid-state quantum simulators. See, P. Hemmer, Science 339, 529 (2013); C. A. Palma and P. Samori, Nat. Chem. 3, 431 (2011) J. Cai, et al., Nat. Phys. 9, 168 (2013). Performing conventional MRI on sub-micron length scales, however, is not possible with present systems and methods because macroscopically generated magnetic-field gradients limit spatial resolution, and inductive detection schemes suffer from significant thermal noise.

Great progress has been made using scanning-probe-based magnetic gradient techniques, which enable nanoscale MRI using ultrasensitive force detection at cryogenic temperatures or fluorescence measurements of optically 'bright' spins such as nitrogen vacancy (NV) color centers in diamond." See, J. A. Sidles, et al., "Magnetic resonance force microscopy," Rev. Mod. Phys. 67, 249 (1995); G. Balasubramanian, I. Y. Chan, R. Kolesov, M. Al-Hmoud, J. Tisler, C. Shin, C. Kim, A. Wojcik, P. R. Hemmer, A. Krueger, T. Hanke, A. Leitenstorfer, R. Bratschitsch, F. Jelezko, and J. Wrachtrup, Nature 455, 648 (2008); C. L. Degen, M. Poggio, H. J. Mamin, C. T. Rettner, and D. Rugar, Proc. Nat. Acad. Sci. 106, 1313 (2009); D. Rugar, R. Budakian, H. J. Mamin, and B. W. Chui, Nature 430, 329 (2004); M. S. Grinolds, P. Maletinsky, S. Hong, M. D. Lukin, R. L. Walsworth, and A. Yacoby, Nat. Phys. 7, 687 (2011). However for most MRI applications, measurements must be taken near room temperature, and nearly all targets of interest contain optically 'dark' spins that are unpolarized or weakly polarized.

SUMMARY OF THE INVENTION

The present invention is a method and system for magnetic resonance imaging that provides sub-nanometer spatial resolution in three dimensions, with single electron-spin sensitivity. The present imaging method and system works under ambient conditions and can measure ubiquitous 'dark' spins, which constitute nearly all spin targets of interest and cannot otherwise be individually detected. In this technique, the magnetic fluctuations of dark spins is measured using a single nitrogen-vacancy (NV) magnetometer located near the surface of a diamond chip. The spatial distribution of spins surrounding the NV magnetometer is imaged with a scanning magnetic-field gradient. The present method and system is compatible with numerous developed methods for bringing imaging targets sufficiently close for NV magnetic detection, and extends the reach of nanoscale MRI to previously in-accessible systems in both the physical and life sciences.

In a preferred embodiment, the present invention is a method for performing three-dimensional magnetic resonance imaging of a sample using a diamond having at least one shallowly planted nitrogen-vacancy (NV) center. The diamond is in the focus of a confocal microscope. The imaging has sub-nanometer resolution on target dark electronic spins in the sample under ambient conditions. The method comprises the steps of applying a driving radio-frequency signal to the sample, applying a microwave signal to the NV center and applying a magnetic-field gradient to the sample with a scanning magnetic tip. The magnetic field gradient provides a narrow spatial volume in which the dark electronic spins in the sample are on resonance with the driving radio-frequency field. The method further comprises the steps of controllably scanning the sample by moving the magnetic tip to a plurality of different positions relative to the sample to systematically bring non-resonant target dark spins in the sample into resonance with the radio-frequency signal and measuring the dark spins by detecting magnetic resonance of the NV center at each of the different magnetic tip positions. The method may further comprise the step of generating a sub-nanometer 3D mapping of a distribution of the dark electronic spins near the NV center. Still further, the point-spread-function for imaging said dark spins is directly measured by the NV center.

To evaluate the performance of the NV-MRI technique, the three-dimensional landscape of dark electronic spins at and just below the diamond surface was imaged and achieve an unprecedented combination of resolution (0.8 nm laterally and 1.5 nm vertically) and single-spin sensitivity. The measurements uncover previously unidentified electronic spins on the diamond surface, which can potentially be used as resources for improved magnetic imaging of samples proximal to the NV-diamond sensor. This three-dimensional NV-MRI technique is immediately applicable to diverse systems including imaging spin chains, read-out of individual spin-based quantum bits, and determining the precise location of spin labels in biological systems.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 2A and 2B illustrate scanning gradients with sub-nm MRI resolution. FIG. 2B illustrates continuous-wave ESR magnetometry with an inverse line-width of τ=120 ns. Specifically, FIG. 2B is a magnetic-tip scan with a 20-nm vertical offset from the NV, zoomed into one resonant slice with a full-width-at-half-maximum of 2.5° A and thus a 12 G/nm tip-induced magnetic-field gradients.

FIGS. 3A-D are MRI ensembles of dark spins at the diamond surface.

DETAILED DESCRIPTION OF THE PREFERRED EMBODIMENTS

The method and system of the present invention combine an NV magnetometer with scanning magnetic-field gradients using an atomic-force microscope. An exemplary NV magnetometer is described in U.S. Pat. No. 8,547,090, entitled "Electron Sin Based Enhancement of Magnetometer Sensitivity." In a preferred embodiment of the present invention, individual shallowly implanted NV centers (nominal depth of 10 nm) are placed in the focus of a confocal microscope so that the NV electronic spin can be initialized by optical pumping, used as a sensor to measure nearby dark spins, and read out using time-dependent fluorescence. See, A. Gruber, et al., "Scanning Confocal Optical Microscopy and Magnetic Resonance on Single Defect Centers," Science 276, 2012 (1997). To image the 3D distribution of dark spins via NV-MRI, a local magnetic-field gradient is applied with a scanning magnetic tip. The magnetic tip provides a narrow spatial volume (a 'resonant slice') in which dark spins are on resonance with a driving radio-frequency (RF) field. Only dark spins within the resonant slice are RF-driven, and thus contribute, to the dark-spin magnetic signal measured by the NV center. The 3D position of the resonant slice is then controllably scanned throughout the sample with angstrom precision by moving the magnetic tip, allowing high-resolution 3D MRI of target dark spins.

To create 3D magnetic resonance images, the detected NV-MRI signal at each magnetic tip position is made conditional on the resonant RF-driving of target dark spins via double electron-electron resonance (DEER). See, B. Grotz, et al., "Sensing external spins with nitrogen-vacancy diamond," New J. Phys. 13 055004 (2011); H. Mamin, et al., "Nanoscale nuclear magnetic resonance with a nitrogen-vacancy spin sensor," Science 339, 557-560 (2013); G. de Lange, et al., "Controlling the quantum dynamics of a mesoscopic spin bath in diamond," Sci. Rep. 2 (2012); and R. G. Larsen and D. J. Single, "Double electron-electron resonance spin-echo modulation: Spectroscopic measurement of electron spin pair separations in orientationally disordered solids," J. Chem. Phys. 98, 5134-5146 (1993). As illustrated in FIG. 1B, microwave (MW) pulsing on the NV spin prepares a coherent superposition of NV-spin states with phase $\phi NV$ that evolves with evolution time $\tau NV$ in proportion to the local magnetic field (projected along the NV quantization axis) from the target dark spins (BDark). Halfway through $\tau NV$, simultaneous MW and RF $\pi$-pulses are applied to the NV and target dark spins respectively, so that $\phi NV$ accumulates only for resonant dark spins, and refocuses for off-resonant dark spins. Target dark spins are in an unpolarized mixed state at room temperature, and so across multiple spin measurements, $<\phi NV>=0$; however, DEER measures $\cos \phi NV$, which is independent of the dark spins' initial states and consequently measures the variance of the dark spins (coming from magnetic quantum-projection noise).

When scanning the magnetic tip to perform NV-MRI, the applied MW signal is simultaneously frequency-locked to the NV spin resonance, which keeps the NV sensor active and also measures the tip-induced frequency detuning. See, R. S. Schoenfeld and W. Harneit, "Real time magnetic field sensing and imaging using a single spin in diamond," Phys. Rev. Lett. 106, 030802 (2011). The resulting spatial map of the frequency-locked NV signal experimentally determines the point-spread-function (PSF) for dark-spin imaging. Because dark spins are spatially offset from the NV location and/or distributed over a non-zero volume, the observed dark-spin signal as a function of magnetic tip position is off-set and/or broadened from the measured PSF, and the dark-spin spatial distribution can be found via deconvolution (see FIG. 1C).

An important feature of the present method and system is that by directly measuring the dark-spin PSF there is no reliance on magnetic-field modeling or iterative deconvolution schemes that must be simultaneously solved for both an unknown signal and an unknown PSF. The spatial resolution of NV-MRI is given by $$\frac{1}{\tau \gamma |\nabla B_{tip}|}$$

where $\gamma$ and $\tau$ are the target spin's gyromagnetic ratio and spin-interrogation time, respectively, and $\nabla Btip$ is the gradient of the tip's magnetic field at the target spin's position projected along the spin's quantization axis.

Figure 1A:
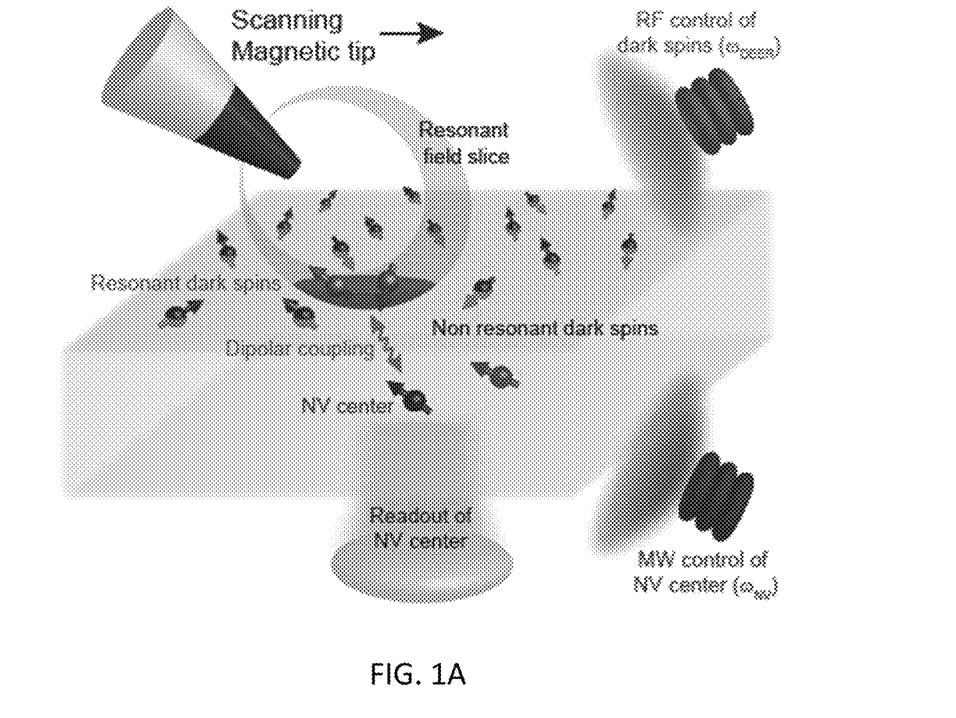
FIG. 1A is a schematic of NV-MRI technique depicting an NV center in a diamond situated in a confocal laser spot with nearby dark spins. A scanning magnetic tip is placed within 100 nm of the diamond surface. Applied microwave (MW) and radio frequency (RF) signals allow for independent coherent control of the NV spin and dark spins. By scanning the magnetic tip, non-resonant dark spins (shown in black) are systematically brought into resonance with the RF signal (resonant spins shown in blue) and are measured via optically detected magnetic resonance of the NV sensor.
Figure 1B:
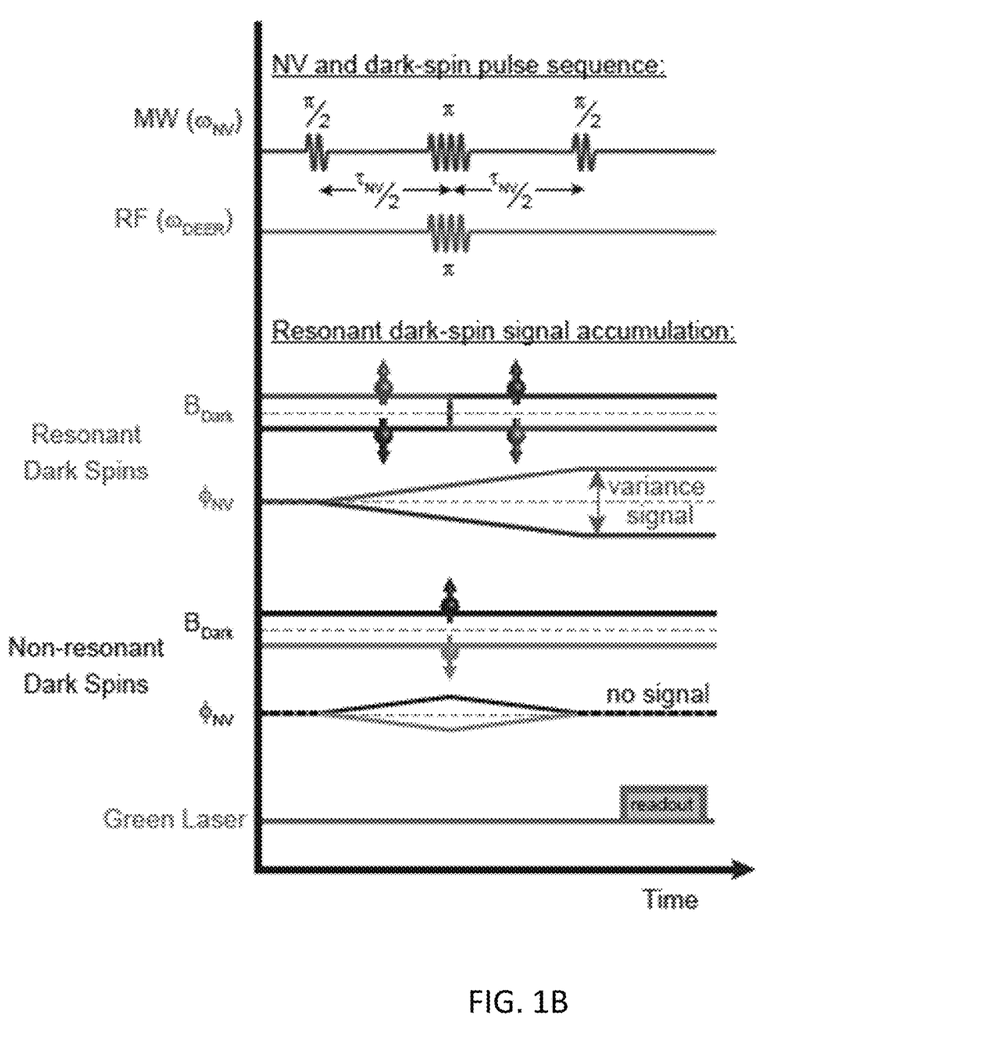
FIG. 1B shows double electron-electron resonance (DEER) pulse sequences executed at each magnetic tip position in a preferred embodiment of the present invention. An MW spin-echo sequence is executed on the NV sensor. By synchronizing an RF π pulse on the dark spins with the MW π pulse in the echo sequence, the time-varying magnetic field from the dark spins (BDark) in the resonant slice (light/dark blue) leads to net NV spin phase (τNV) accumulation, while the magnetic field from non-resonant dark (grey/black) spins is refocused and thus their effects on the NV spin are cancelled, irrespective of the initial polarization state of the dark spins.
Figure 1C:
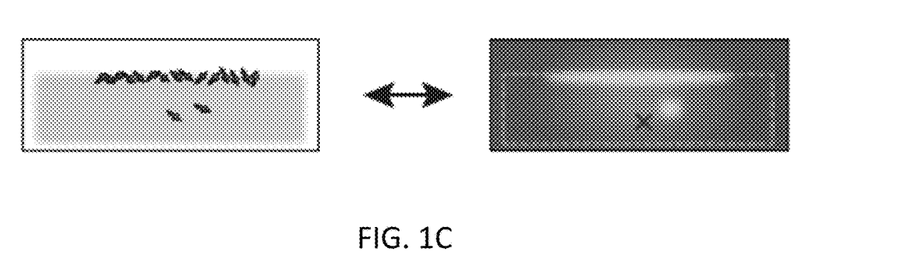
FIG. 1C illustrates imaging of the distribution of spins around the NV. NV-MRI provides 3D mapping of the distribution of dark electronic spins near the NV sensor (indicated by the second cross), with sub-nanometer resolution.
Figure 2A:
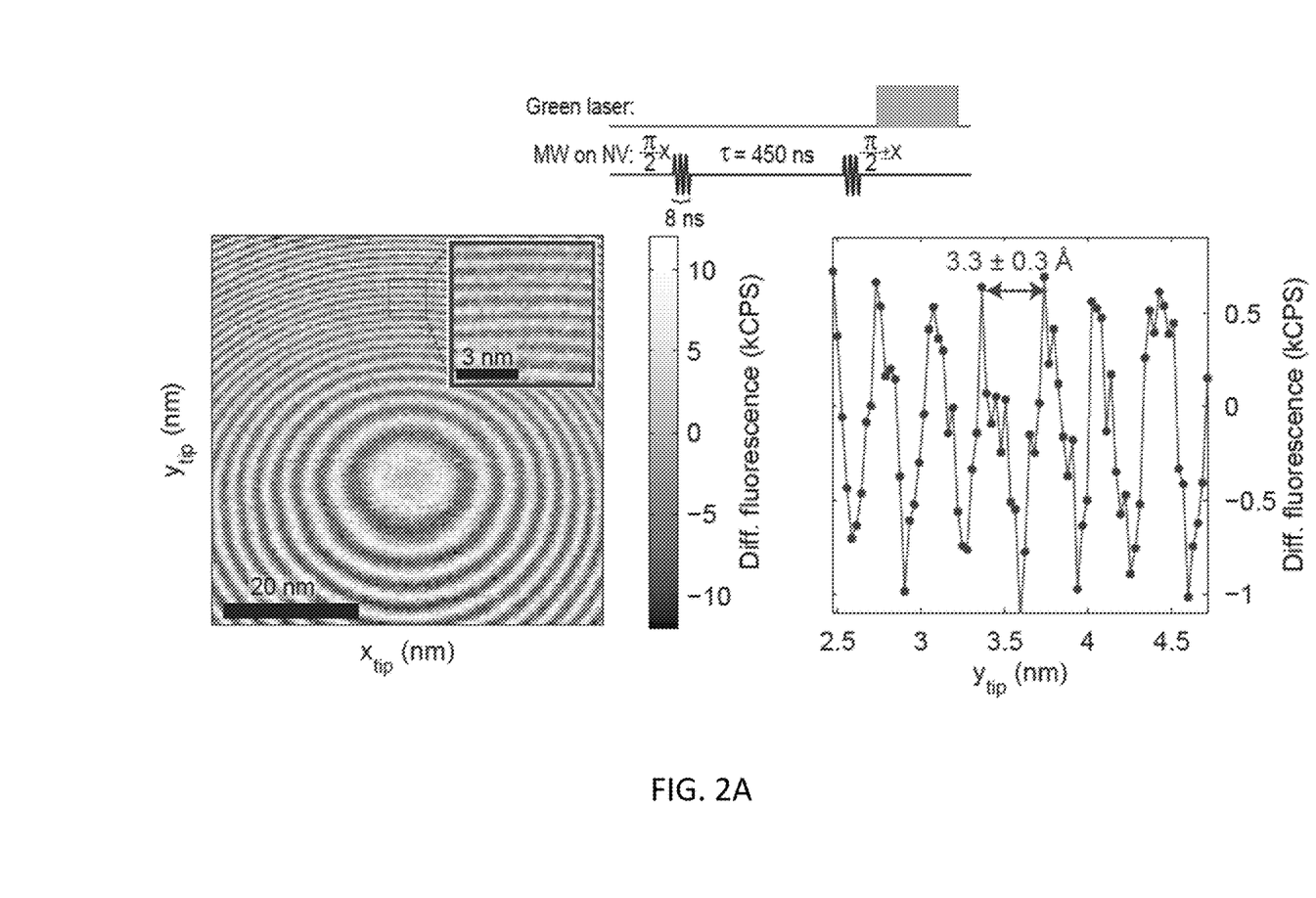
FIG. 2A illustrates scanning Ramsey interferometry on a single, shallow NV center in a 0.12-T external magnetic field. As the magnetic tip is laterally scanned over the NV center 50 nm above the diamond surface and near the NV center, the resultant variation in magnetic field at the NV center leads to 2D spatial oscillations in the measured NV Ramsey interferometry fluorescence signal as a function of lateral tip position (center panel). A line cut along the y-direction (30 nm above the diamond surface, right panel) shows oscillations with a period of 3.3±0.3° A, indicating that the tip-induced magnetic-field gradients are 2.4 G/nm.
Figure 2B:
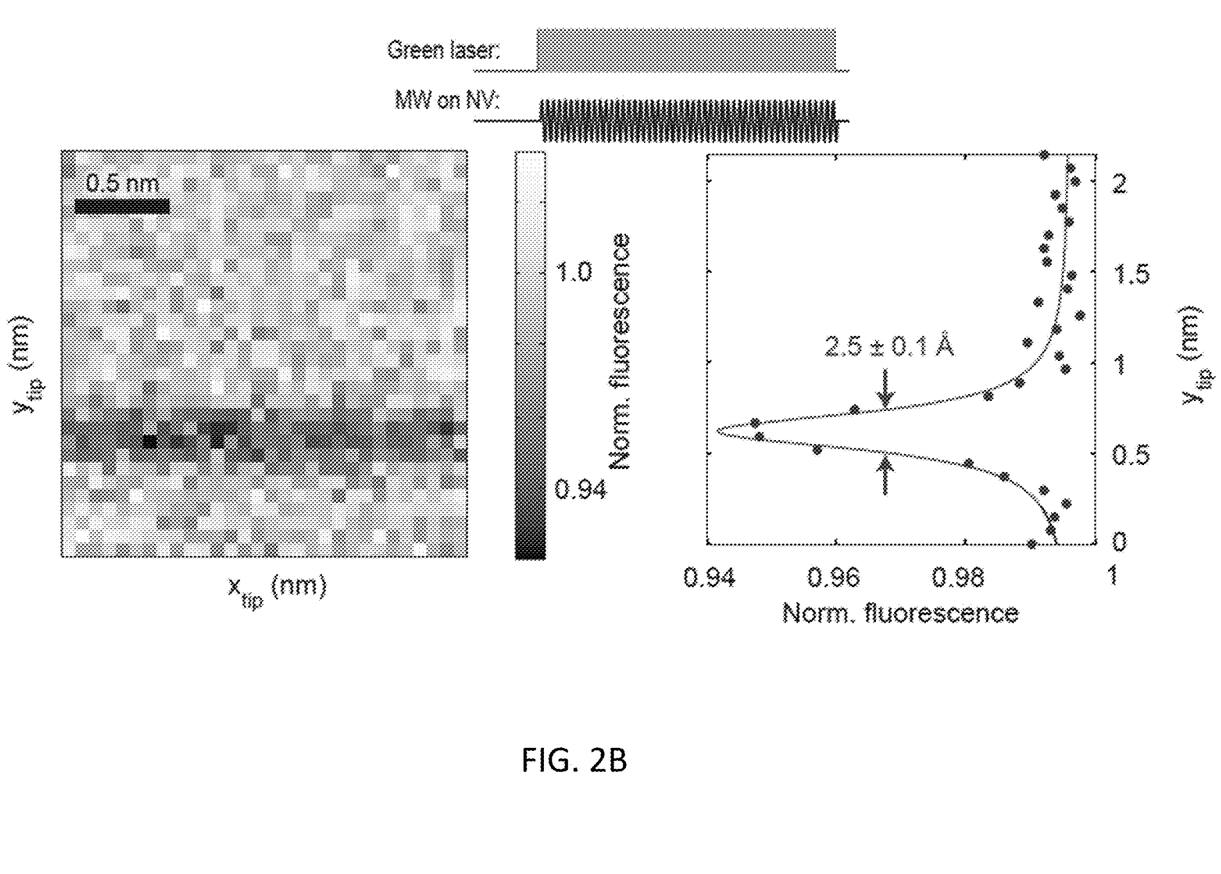

An experimental setup is shown in FIG. 1A. The spatial resolution limit in the setup was determined by measuring $\nabla Btip$ using a single NV center, with a relatively long $T^*$ coherence time, which allows for a long $\tau$. Using a $\tau=450$ ns Ramsey interferometry sequence, spatial fringes were measured with oscillation periods down to $3.3\pm0.3°$ A (see, FIG. 2A), demonstrating that the experimental setup is mechanically stable down to sub-nm length scales. By bringing the tip closer to the NV center, gradients of at least 12 G/nm (effective $\tau=120$ ns) were observed (see, FIG. 2B); however, vibrations in the experimental setup limited the spatial resolution to $2.5°$ A. For NV-MRI of dark spins with static tip gradients, the target-spin interrogation time is limited the target spin $T^*(150$ ns), enabling sub-nanometer 3D NV-MRI resolution.

To demonstrate such sub-nanometer NV-MRI performance, the spin environment of individual NV centers near a diamond surface were spatially mapped. Shallow NV centers are the mainstay for NV-based sensing and quantum-information processing, yet their dominant sources of decoherence have not been identified and localized. In the absence of the magnetic tip, used DEER spectroscopy was used first to observe a g=2 dark electronic spin bath coupled to shallow NV spins, consistent with previous measurements that did not determine the origin or spatial distribution of these dark spins. See, H. J. Mamin, et al., "Detecting external electron spins using nitrogen-vacancy centers," Phys. Rev. B 86, 195422 (2012). In the example, g=2 electron-spin resonances for more than 60% of measured NV spins (>30 centers in three diamond samples) were measured. The NV-MRI technique was then used to perform 3D imaging of the spatial distribution of these dark electronic spins on and near the diamond surface.

Figure 3A:
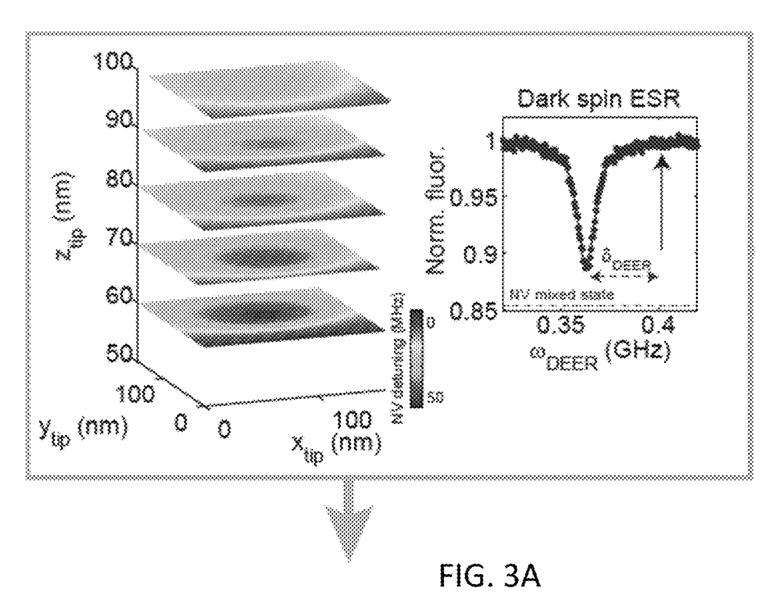
FIG. 3A illustrates determining the dark-spin NV-MRI point-spread function (PSF). 3D plot of the detuning of the frequency-locked NV microwave signal ωNV, is measured by xy scanning of the magnetic tip with variable z offset of 60 nm to 100 nm from the diamond surface (left). This detuning map is combined with the tip-independent dark-spin electron-spin resonance (ESR) spectrum (right) to determine the dark-spin PSF.
Figure 3B:
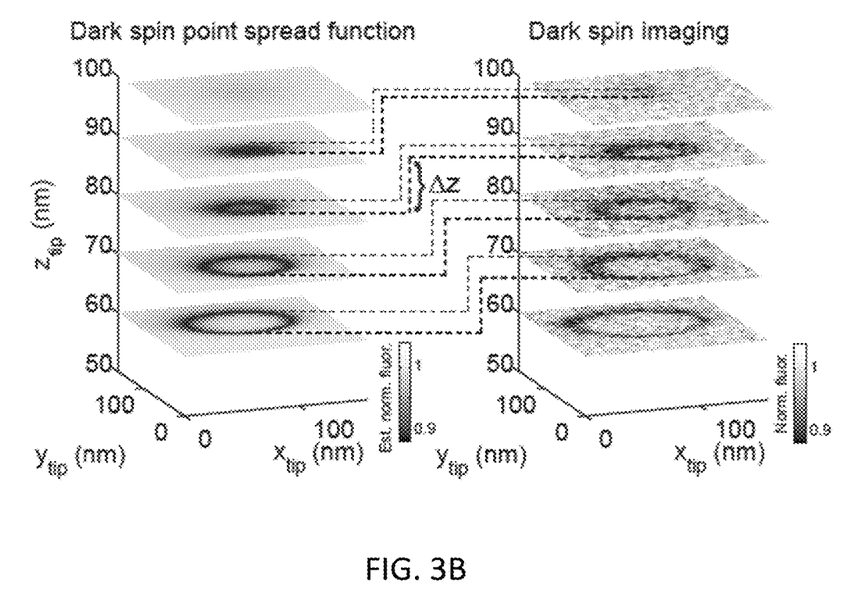
FIG. 3B shows NV-MRI tomography of dark spins proximal to an individual shallow NV center. Displacement of the dark-spin resonance slice image (right) from the dark-spin PSF (left) indicates the location of the dark spins with respect to the NV center. For a given dark-spin lateral (xy) image, the best match to the dark-spin PSF (determined from the diameter of the resonance circle) is shifted by Δz=10 nm, showing that the dark spins lie at or very close to the diamond surface.
Figure 3C:
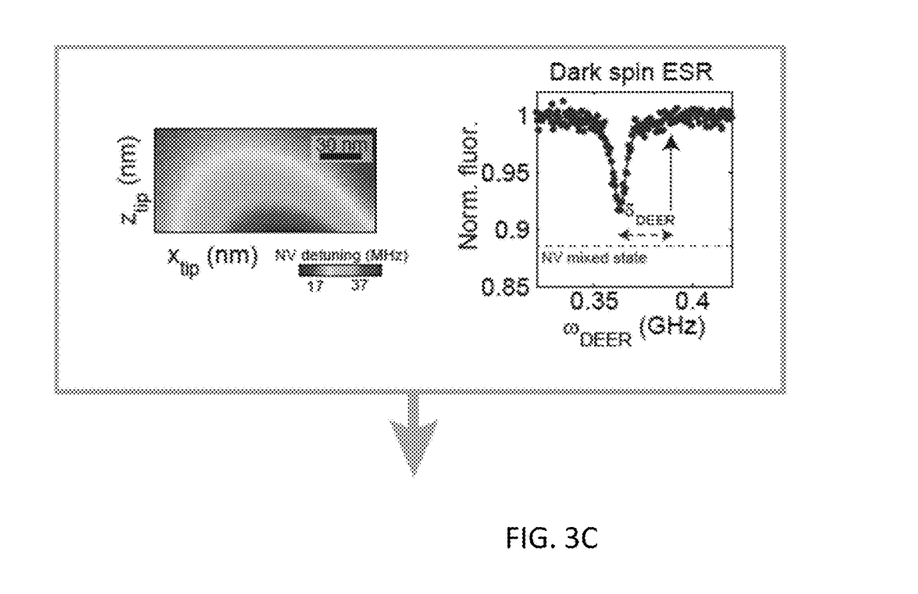
FIG. 3C shows dark-spin PSF determination for a second NV center in a vertical (xz) scan.
Figure 3D:
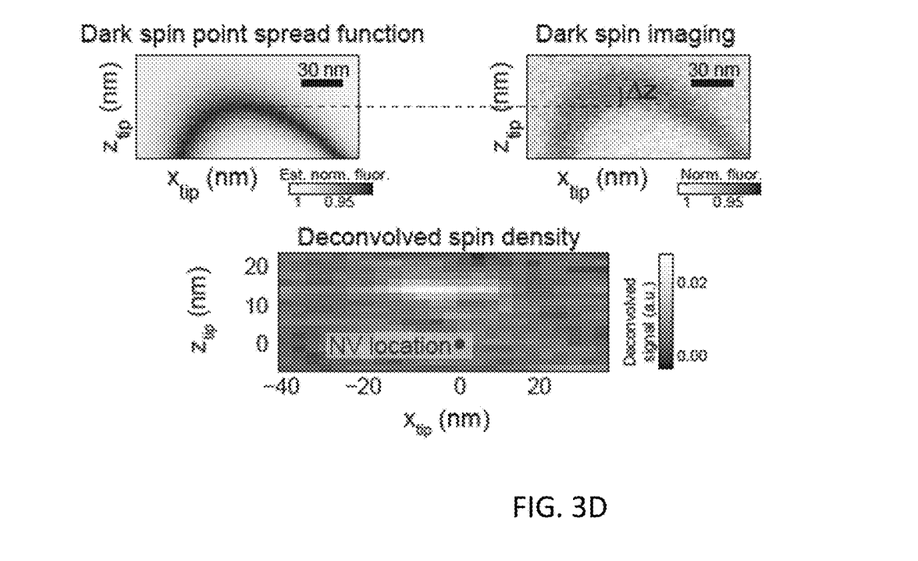
FIG. 3D shows vertical (xz) NV-MRI of dark spins. Similar to FIG. 3B, the dark-spin resonance slice image is vertically shifted (Δz=14 nm for this NV sensor), again suggestive of surface dark spins. De-convolving the dark-spin image with the PSF gives the spatial distribution of the nearby dark spins, indicating a surface layer above the shallow NV center.

Imaging experiments mapping the spatial locations of these g=2 dark spins around two separate NV centers are presented by scanning the magnetic tip in three dimensions (FIGS. 3A-3D). Comparing the measured dark-spin PSF to the observed dark-spin resonance slice (FIGS. 3B and 3D), we find that for both NV centers the dark-spin signal is shifted vertically from the PSF, which shows that the imaged dark spins are located 10 nm and 14 nm above the two NV sensors, respectively (FIGS. 3B and 3D). Given the implantation energy used to form the shallow NV spins, the observed dark-spin location is consistent with them being on the diamond surface (nominal depth of 10±3 nm).

An image deconvolution along the xz plane (FIG. 3D) directly shows that the dark spin distribution is spread out in a line, indicating a layer of spins at the diamond surface. This layer of dark spins likely extends further in the xz plane direction, probably with near-uniform coverage over the diamond surface, but laterally distant spins couple more weakly to the single NV and are undetectable when their signal becomes smaller than the measurement noise. As present invention directly measures the vertical distance between the NV sensor and the dark-spin layer, the density of dark spins in the layer can be found using the dark-spin/NV coupling rate (100 kHz for this NV center). See B. K. Ofori-Okai, et al., "Spin properties of very shallow nitrogen vacancy defects in diamond," Phys. Rev. B 86, 082413 (2012). The extracted two-dimensional dark-spin density is 0.5 spins/nm2, which for a surface layer corresponds to a single unpaired electron spin every 60 surface atoms.

Figure 4A:
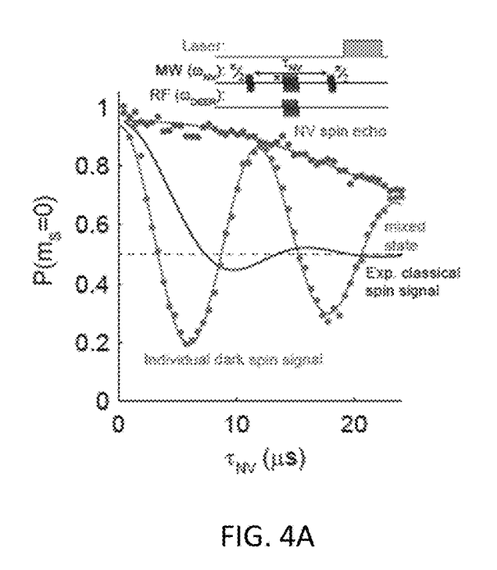
FIG. 4A shows coherent dynamics from an individual dark spin strongly coupled to a single shallow NV center. Measured oscillations in the NV DEER signal (pulse sequence shown at top) as a function of spin evolution time τNV. The DEER signal oscillates coherently and overshoots the NV mixed state, indicated strong coupling of the NV to a single nearby dark electronic spin. For comparison, the expected DEER signal is plotted (black solid line) for comparably strong NV coupling to a single classical spin, demonstrating that the dark-spin effect on the NV DEER signal originates from quantum-projection noise.

It also was observed that some shallow NV spins are coherently coupled to an individual dark electronic spin, as evidenced by coherent oscillations in the DEER signal as a function of evolution time (FIG. 4A). See, F. Shi, et al., "Quantum logic readout and cooling of a single dark electron spin," Phys. Rev. B 87, 195414 (2013). Note that the intensity of the observed dark-spin DEER oscillations cannot be explained by a classical single spin, where the spin is modeled by a magnetic moment that can have an arbitrary, continuous magnetization. In that situation, for an un-polarized dark spin, the measured DEER signal would average over all possible magnetizations and the signal would decay to the NV mixed state. However, for a S=½ quantum spin, measurement of its magnetization can only yield two values, giving single-frequency oscillations in the DEER signal, as we observe. This quantum-projection noise enhances the signal for MRI imaging, and in this case it increases the signal-to-noise of dark-spin imaging by 1.9 compared to a classical variance.

Figure 4B:
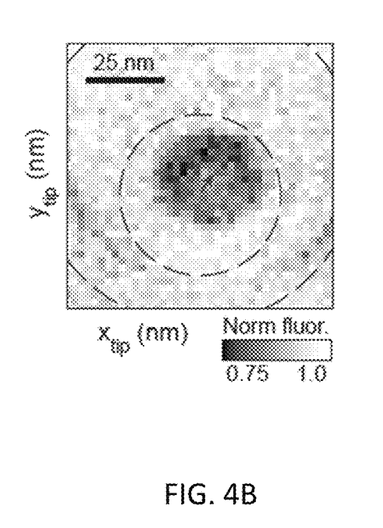
FIG. 4B shows lateral (xy) NV-MRI of single, coherently coupled dark spin at 50-nm z-axis tip offset; the dark-spin PSF is illustrated in dashed red lines. The vector connecting the center of the PSF circle and the dark-spin resonance gives the lateral shift (Δx,Δy) of the dark spin from the NV. Two distinct resonant slices appear because different sets of dark-spin hyperfine transitions are driven by the applied RF signal.
Figure 4C:
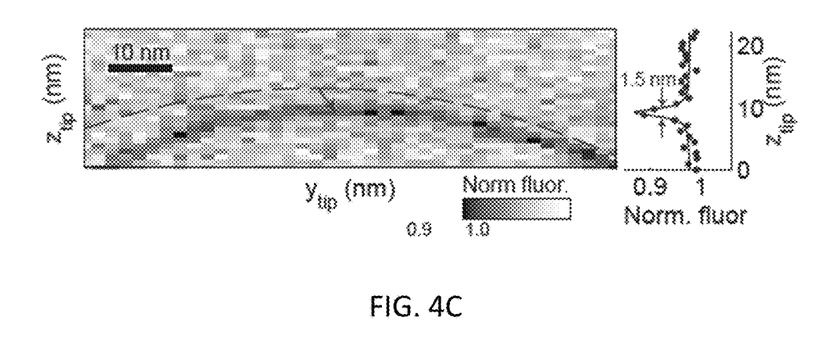
FIG. 4C shows vertical (yz) NV-MRI of the same coherently coupled dark spin as shown in FIG. 4B. Scanning the magnetic tip across the symmetry plane of the lateral image in b gives the dark-spin vertical shift Δz, in addition to a second measure of Δy. The tip-induced magnetic-field gradient along the z-direction provides 1.5 nm spatial resolution.
Figure 4D:
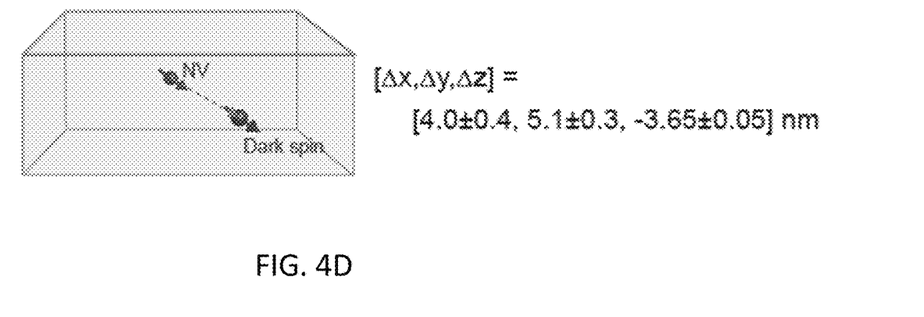
FIG. 4D is an illustration of the 3D location of the coherently coupled dark spin relative to the NV sensor, as determined from data in b,c.
Figure 4E:
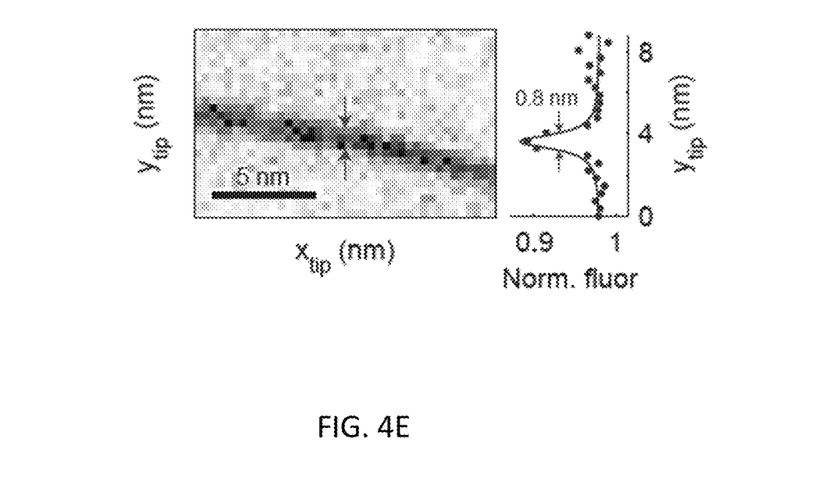
FIG. 4E is a lateral (xy) NV-MRI of a second coherently coupled dark spin, imaged with 0.8 nm resolution.

Next, we imaged the 3D location of this coherently coupled dark spin by scanning the magnetic tip both laterally (FIG. 4B) and vertically (FIG. 4C) and using the deconvolution method described in FIGS. 3A-3D. For vertical imaging, we found an offset of the dark-spin position relative to the NV sensor of $[\Delta y, \Delta z]=[5.1\pm0.3, -3.65\pm0.05]$ nm, with spatial resolution of $1.5\pm0.6$ nm given by the spatial width of the dark-spin resonance. For lateral imaging, the dark-spin signal is not only shifted in location, but is also different in size because the dark spin lies at a different depth than the NV sensor and magnetic field gradients along the z direction are strong compared to the lateral gradients. To achieve high-precision spin-localization in the lateral dimensions, we fit the center of mass of the measured dark-spin PSF and compared this PSF to the center of the response circle, yielding the lateral offset $\Delta x=4.0\pm0.4$ nm. The location of this coherently coupled dark spin relative to the NV sensor is illustrated in the cartoon in FIG. 4D. As an additional example, FIG. 4E displays an xy-plane NV-MRI image of another dark-spin that is coherently coupled to a different NV spin. The lateral spatial resolution in this image is $0.8\pm0.4$ nm, and we observe that its location is consistent with being potentially on the diamond surface.

Our NV-MRI demonstration provides the first 3D spatial mapping of dark electronic spins on and near a diamond surface, achieving sub-nanometer resolution. We expect that NV-MRI will be applicable to a wide range of systems in both the physical and life sciences that can be placed on or near the diamond surface and then probed under ambient conditions. For example, one-dimensional spin chains have been proposed as a method for transfer-ring quantum information [25]. A key technical challenge that NV-MRI could address is determining the precise (atomic-scale) location of spins along a chain, which critically influences the fidelity of quantum information transfer. Additionally, individual paramagnetic electron spins with long coherence times at room temperature have attracted interest as potential quantum bits [26], but currently such spins cannot be read out individually. NV-MRI would allow for simultaneous control and detection of dark electron spins brought into proximity to NV sen-sors near the diamond surface. Finally, NV-MRI could image the location of individual electronic spin labels in biological systems, e.g., selectively attached to specific amino acids on a protein [27], which could aid in the determining the structure of proteins.

Furthermore, studying the nanoscale electronic environment on and near diamond surfaces is critical for understanding and maximizing the coherence of NV sensors and quantum bits. We find that the majority of dark spins near shallow NV centers are at the diamond surface, and thus we expect that passivation of the surface to reduce the dark-spin density will im-prove NV-based sensing and quantum information applications. Alternatively, dark spins at the surface could be initialized with NV-assisted spin-polarization techniques [28, 29] and then used as a resource for improved sensing: such ancilla sensor spins would effectively amplify magnetic signals [30] from samples placed on [13, 15] or scanned [11, 20] over the diamond surface. In addition, coherently coupled dark spins, which we identified and imaged can potentially be entangled with the NV sensor to achieve Heisenberg-limited sensing [31], thus dramatically increasing metrology performance.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for performing three-dimensional magnetic resonance imaging of a sample using a diamond having at least one shallowly planted nitrogen-vacancy center, wherein said diamond is in the focus of a confocal microscope, said imaging having sub-nanometer resolution on target dark electronic spins in said sample under ambient conditions, comprising the steps of:
    applying a driving radio-frequency signal to said sample;
    applying a microwave signal to said nitrogen-vacancy center;
    applying a magnetic-field gradient to said sample with a scanning magnetic tip, wherein said magnetic field gradient provides a narrow spatial volume in which said dark electronic spins in said sample are on resonance with said driving radio-frequency field;
    controllably scanning said sample by moving said magnetic tip to a plurality of different positions relative to said sample, thereby systematically bringing non-resonant target dark spins in said sample into resonance with said radio-frequency signal;
    measuring said dark spins by detecting magnetic resonance of said nitrogen-vacancy center at each of said different magnetic tip positions.

2. The method for performing three-dimensional magnetic resonance imaging of a sample according to claim 1, further comprising the step of generating a 3D mapping of a distribution of said dark electronic spins near said nitrogen-vacancy center, said 3D mapping having sub-nanometer resolution.

3. The method for performing three-dimensional magnetic resonance imaging of a sample according to claim 1, further comprising the step of directly measuring a dark-spin point-spread-function for imaging said dark spins.

4. The method for performing three-dimensional magnetic resonance imaging of a sample according to claim 3, wherein said step of directly measuring a point-spread function comprises the steps of:

simultaneously frequency-locking the applied microwave signal to a spin resonance of said nitrogen-vacancy center and measuring a magnetic tip-induced frequency detuning;

generating a spatial map of said magnetic tip-induced frequency detuning to determine a point-spread-function for imaging of said dark spins.

5. The method for performing three-dimensional magnetic resonance imaging of a sample according to claim 1, wherein said step of applying a microwave signal to said nitrogen-vacancy center comprises executing a microwave spin-echo sequence on the nitrogen-vacancy center; wherein said microwave spin-echo sequence is synchronized with said radio-frequency signal.

6. The method for performing three-dimensional magnetic resonance imaging of a sample according to claim 1, wherein the detected magnetic resonance at each said different tip position is made conditional on said applied driving radio-frequency signal by double electron-electron resonance.

* * * * *